United States Patent [19]

Hanma et al.

[11] 3,978,053
[45] Aug. 31, 1976

[54] PROCESS FOR PRODUCING CEPHALOSPORINS

[75] Inventors: Noritaka Hanma, Sakai; Masataka Fukumura, Toyonaka; Kaoru Maeshima, Takarazuka; Takenari Nakagome, Nishinomiya, all of Japan

[73] Assignee: Sumitomo Chemical Company, Limited, Osaka, Japan

[22] Filed: Nov. 29, 1974

[21] Appl. No.: 528,313

[30] Foreign Application Priority Data

Nov. 29, 1973 Japan............................ 48-135056

[52] U.S. Cl............................ 260/243 C; 424/246
[51] Int. Cl.² ....................................... C07D 501/02
[58] Field of Search .............................. 260/243 C

[56] References Cited
UNITED STATES PATENTS

| | | | |
|---|---|---|---|
| 3,725,397 | 4/1973 | Graham et al. ............ | 260/243 C |
| 3,725,399 | 4/1973 | Ellerton et al. ............ | 260/243 C |
| 3,843,637 | 10/1974 | Rubinfeld et al. ......... | 260/243 C |
| 3,852,281 | 12/1974 | Verweij ...................... | 260/243 C |

*Primary Examiner*—Nicholas S. Rizzo
*Attorney, Agent, or Firm*—Sughrue, Rothwell, Mion, Zinn & Macpeak

[57] ABSTRACT

A process for producing a compound of the formula (I)

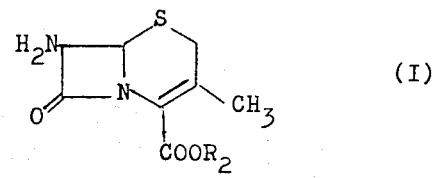

wherein $R_2$ is a hydrogen atom or an ester protective group, which is useful as a precursor for the production of cephalosporin derivatives, comprising reacting a phosphoramide derivative of cephalosporin of the formula (II)

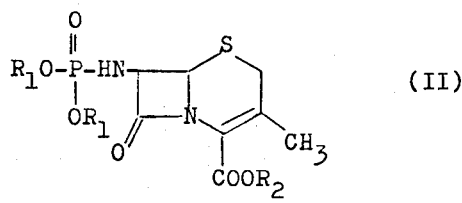

wherein $R_1$ is a lower alkyl group and $R_2$ is as defined above, with a phosphorus acid. A further embodiment includes preparing the phosphoramide derivative of cephalosporin of the formula (II) by reactng a compound of the formula (III)

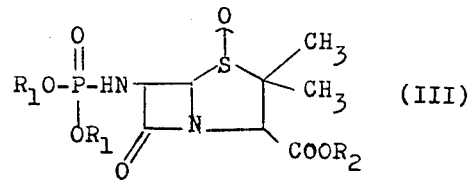

wherein $R_1$ and $R_2$ are as defined above, with an acid compound.

22 Claims, No Drawings

PROCESS FOR PRODUCING CEPHALOSPORINS

BACKGROUND OF THE INVENTION

1. Field of the Invention

The present invention relates to a process for producing a cephalosporanic acid derivative, and more particularly to a process for producing a cephalosporanic acid derivative from a cephalosporanic phosphoramide.

2. Description of the Prior Art

The cephalosporanic acid derivative of the formula (I) can be obtained, as disclosed in U.S. Pat. No. 3,275,626, by conversion of a 1-oxide derivative of 6-acylamidopenicillin to obtain the corresponding 7-acylamidocephalosporin derivative followed by a deacylation of the resulting 7-acylamidocephalosporin derivative, as disclosed in U.S. Pat. No. 3,549,628. The deacylation, however, gives rise to many problems which render it difficult to carry out the acylation on an industrial scale, that is, it is essential to isolate and purify the 7-acylamidocephalosporin because the yield of the desired compound of the formula (I) is remarkably influenced by the purity of the 7-acylamidocephalosporin and, in addition, the reaction system must strictly be controlled so as to maintain anhydrous conditions.

SUMMARY OF THE INVENTION

An object of the present invention is to provide a process for preparing cephalosporanic acid derivatives of the formula (I) which does not have the disadvantages of prior art preparation processes.

The invention provides a process for producing a cephalosporanic acid derivative represented by the formula (I)

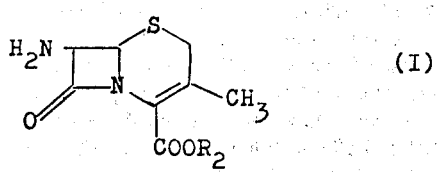

(I)

wherein $R_2$ is a hydrogen atom or an ester protective group which comprises reacting a phosphoramide derivative of cephalosporin represented by the formula (II)

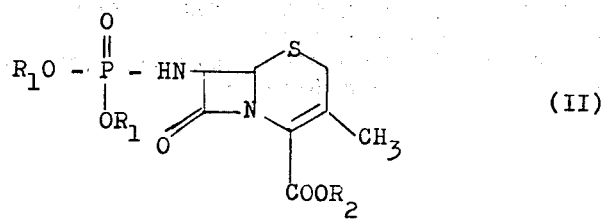

(II)

wherein $R_1$ is a lower alkyl group and $R_2$ is as defined above, with a phosphorus acid.

A further embodiment of this invention provides a process for preparing the phosphoramide derivative of cephalosporin of the formula (II) by reacting a compound of the formula (III)

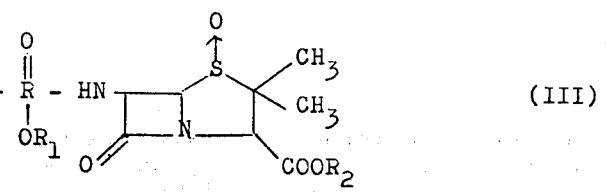

(III)

wherein $R_1$ and $R_2$ are as defined above with an acid compound.

DETAILED DESCRIPTION OF THE INVENTION

The compounds represented by the formula (I) are useful as precursors for the production, for example as disclosed in U.S. Pat. Nos. 3,507,861 and 3,549,628 of cephalosporin compounds, such as cephalexin, having a broad spectrum of antimicrobial activity. Processes for preparing these useful compound have been studied and as a result this invention provides a superior method by which the desired compound (I) can be readily obtained from the phosphoramide derivative of cephalosporin of the formula (II).

The process according to the present invention in contrast to the prior art method described above comprises heating a 1-oxide derivative of 6-dialkylphosphoramido penicillanic acid to produce a cephalosporin derivative (II), and adding a phosphorus acid to the resulting derivative (II) with or without isolating the resulting derivative the desired compound (I) can be obtained industrially advantageously.

According to the method of the present invention, the desired compound of the formula (I) can be obtained in a high purity and high yield by treating the compound of the formula (II) with a phorphorus acid whereby the phosphorus-nitrogen linkage is selectively cleaved without any disadvantageous side reactions such as decomposition of the β-lactam ring.

Furthermore, the process of the present invention is also useful for purification of the cephalosporin derivative of the formula (I). That is, a compound of the formula (I) of low purity can be purified into that of high purity, by converting the compound of the formula (I) to the dialklphosphoramido compound of the formula (II), and then treating the resulting compound of the formula (II) with a phosphorus acid according to the present invention.

The compound of the formula (I) thus obtained can be acylated with a respective acylating agent to obtain the corresponding cephalosporin derivative. In this way, the process according to the present invention can be applied advantageously to the preparation of a 7-acylamidocephalosporin derivative.

According to the present invention, the cephalosporanic acid derivative of the formula (I)

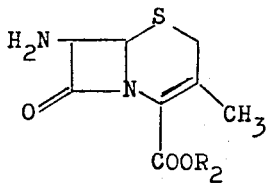

(I)

wherein $R_2$ is a hydrogen atom or an ester protective group, is produced by treating the phosphoramide derivative of cephalosporin of the formula (II)

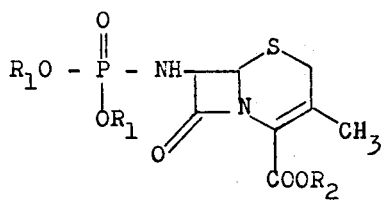

(II)

wherein $R_1$ is a lower alkyl group and $R_2$ is as defined above, with a phosphorus acid.

In the general formula (II), $R_1$ represents a lower alkyl group, e.g., a straight chain or branched chain alkyl group having 1 to 4 carbon atoms such as a methyl, ethyl, isopropyl and n-butyl group, and $R_2$ represents a hydrogen atom or an ester protective group commonly employed in the synthesis of cephalosporin compounds.

Typical examples of such ester protective groups are alkyl groups such as a methyl group, halogenated alkyl groups such as a 2,2,2-trichloroethyl group, aralkyl groups such as a benzyl group, a p-nitrobenzyl group, a p-methoxybenzyl group, a 4-methoxy-3,5-di-tert-butylbenzyl group, a phenacyl group and a benzhydryl group, alkylsulfonylalkyl groups such as a methylsulfonylmethyl group, trialkylsilyl groups such as a trimethylsilyl group, and the like. The ester protective groups and their function are well known in the art and can be freely selected by one skilled in the art so long as the function of protection is achieved.

The term "phosphorus acid" is employed herein to describe phosphorus acid type compounds such as ortho-phosphoric acid, phosphorous acid, phosphonic acid, phosphinic acid, and the ester and anhydride derivatives thereof. Specifically, suitable derivatives include phosphoric esters such as monomethyl phosphate, dimethyl phosphate, monoethyl phosphate, monophenyl phosphate, diphenyl phosphate and monobenzyl phosphate; phosphorous esters such as monomethyl phosphite and monophenyl phosphite; phosphoric acid anhydrides such as pyrophosphoric acid, polyphosphoric acid and phosphorus pentoxide; phosphoric ester anhydrides such as dimethyl pyrophosphate, diphenyl pyrophosphate and polyphosphoric ester; phosphonic acid derivatives such as methylphosphonic acid and phenylphosphonic acid; and phosphinic acid derivatives such as dimethylphosphinic acid and diphenylphosphinic acid. Of these phosphorus acids, ortho-phosphoric acid, phosphorous acid, and polyphosphoric acid are particularly preferred industrially.

In general, the reaction is carried out in a mixture of the compound of the formula (II) and the phosphorus acid in the absence of a solvent, or in a solution or suspension in an inert solvent, such as aromatic hydrocarbons, e.g., benzene, toluene, etc.; chlorinated hydrocarbons, e.g., dichloromethane, chloroform, etc; ethers, e.g., dioxane, diethyl ether, etc.; alcohols, e.g., methanol; amides such as dimethylformamide, etc.; dimethylsulfoxide; water; or carboxylic acids such as formic acid, acetic acid, propionic acid, etc.

The reaction suitably proceeds at temperatures above about −20°C, but in general, a temperature range between 0°C and 100°C is preferred for obtaining good results.

The amount of phosphorus acid used in the reaction can vary with the phosphorus acid being present in excess or the compound of the formula (II) being present in excess, but an amount of more than 1 mole per mole of the compound of the formula (II) particularly more than 3 moles is particularly preferred for obtaining good results. And since the phosphorus acid can act as the reaction medium the amount of the phosphorus acid can range up to about 100 to 500 moles per mole of the compound of the formula (II).

When an inert solvent is employed, the amount of the inert solvent is such that the concentration of phosphorus acid is more than about 10% by weight, but a concentration of 50 to 100% by weight (i.e., no solvent) is preferred particularly for obtaining good results.

The manner of isolation of the resulting compound of the formula (I) depends upon the property of the reactants used according to the present invention, but in general it is carried out (1) by neutralizing the reaction system with inorganic or organic alkaline substances, such as sodium bicarbonate, sodium carbonate, sodium hydroxide, ammonia and triethylamine, and then by extracting with inert solvents such as benzene, ethylacetate, diethyl ether and chloroform, or (2) by adding acidic substances capable of forming a salt of the compound of the formula (I) to the reaction system, for example, hydrogen chloride, p-toluenesulfonic acid and β-naphthalenesulfonic acid, without neutralization unlike the former method (1), and then by filtering the precipitated crystals whereby the salt of the desired compound of the formula (I) is obtained in high yield and high purity.

In the present invention, furthermore, when the starting material of the formula (II) is an ester, the desired compound of the formula (I) wherein $R_2$ is a hydrogen atom can be obtained directly with appropriate $R_2$ substituents and treating conditions. In addition, when the desired compound of the formula (I) is an ester, the compound can be converted to a compound in which $R_2$ is a hydrogen atom by removing the ester residue from the compound which may or may not be isolated, as desired.

For instance, when $R_2$ in the formula (II) is an ester protective group which is removable by reduction, for example, 2,2,2-trichloroethyl, benzyl, p-nitrobenzyl, and phenacyl, 3-methyl-7β-amino-ceph-3-em-4-carboxylic acid can be obtained in a high purity and in high yield by reacting the compound of the formula (II) with a phosphorus acid according to the present invention, and then treating the reaction mixture with zinc, as disclosed in *J. Am. Chem. Soc.*, 88, 852 (1966), Tetrahedron Letters, 342 (1970), and German Pat. No. 2,242,684, without isolating the intermediate ester compound of the formula (I).

The compound of the formula (II) which is used as a starting material according to the present invention is a novel compound, not previously described in the literature, and can be produced readily advantageously in the present invention. That is, the compound of the formula (II) can be produced advantageously and readily by heating a phosphoramide derivative of penicillin sulfoxide of the formula (III),

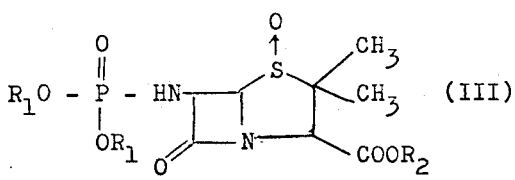

wherein $R_1$ and $R_2$ are as defined above, in the presence of an acid compound.

The conversion of the penicillin sulfoxide derivative of the formula (III) into the compound of the formula (II) can be carried out in an inert solvent, preferably in a solvent which can form an azeotropic mixture with water. Suitable examples of water azeotroping solvents which can be used in the conversion of the compound of the formula (III) into the compound of the formula (II) are aromatic hydrocarbons such as benzene and toluene; aliphatic halogenated hydrocarbons such as dichloroethane; cyclic ethers such as dioxane; nitriles such as acetonitrile; ketones such as methyl isobutyl ketone; tertiary amides such as dimethylformamide and the like.

In this conversion, better results can sometimes be obtained by using a tertiary amide as a solvent for all or a portion of the above inert solvent. Typical examples of suitable tertiary amides are dimethylformamide, dimethylacetamide, etc. Dioxane and a mixture of dichloroethane and dimethylformamide are preferred. A broad range of concentrations can be used and the concentration range employed is not limited. A preferred concentration of the compound of the formula (III) is about 1 to 20% by weight. Although the conversion can be carried out over a wide range of reaction temperatures higher than room temperature (e.g., about 20° to 30°C), it is generally preferred to carry out the conversion at the reflux temperature of the solvent used while azeotropically removing the water formed during the conversion reaction from the reaction system. A particularly preferred temperature range is from about 80° to about 170°C.

The water formed during the reaction can also be removed from the reaction system by treatment with a dehydrating agent such as those generally used in organic syntheses, for example, calcium chloride, magnesium sulfate, calcium oxide, molecular sieves, etc. In this instance, it is advantageous to remove the water from the reaction solvent distilled off as an azeotropic mixture with the above dehydrating agent and then the anhydrous solvent be returned to the reaction system. For this purpose, an apparatus such as Soxhlet extractor, a Dean-Stark trap, etc. can advantageously be used with good results.

The conversion reaction is conducted in the presence of a catalytic amount of an acid compound. Suitable examples of acid compounds which can be used in the conversion reaction are organic acids, for example, organic sulfonic acids such as methanesulfonic acid, para-toluenesulfonic acid, naphthalenesulfonic acid and the like; organic phosphonic acids such as methanephosphonic acid, dichloromethanephosphonic acid and phosphonic acid monoesters such as the monomethyl, monophenyl or 2,2,2-trichloroethyl ester; carboxylic acids having 2 to 5 carbon atoms or the anhydrides thereof, such as acetic acid, propionic acid and the like and the anhydrides of these acids; and mineral acids such as phosphoric acid, sulfuric acid, hydrochloric acid, nitric acid, and the like. In some cases, carboxylic acid anhydrides such as acetic anhydride can be used as the solvent and serve a dual function as the solvent and the acid compound. In addition, the acid compound employed can be a salt of a strong acid and a weak base, e.g., having a pKb greater than about 4, for example, pyridine phosphate, pyridine mono-0-substituted orthophosphate, quinoline hydrochloride and the like. A suitable molar ratio of the acid compound to the amount of the compound of the general formula (III) generally ranges from about 0.001 to 0.5, preferably 0.01 to 0.2. The penicillin sulfoxide derivative represented by the formula (III) is a novel compound, not previously disclosed in the literature, and can be prepared advantageously and conveniently using any one of the following procedures:

Method 1)

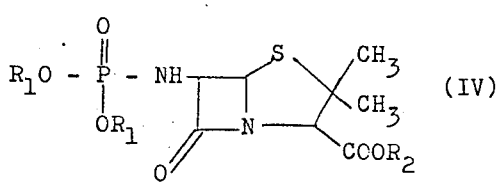

The phosphoramide derivative of penicillin represented by the formula (IV), wherein $R_1$ and $R_2$ are as defined above, can be oxidized with a peroxide in an inert solvent. Suitable peroxides which can be employed in the reaction are, for example, organic peroxides such as peracetic acid, monopermaleic acid, m-chloroperbenzoic acid, and inorganic peroxides such as ozone, sodium periodate, hydrogen peroxide, and the like. The reaction is preferably carried out at relatively low temperature at which decomposition of the β-lactam ring and the peroxide does not occur, but a temperature ranging from about −20°C to room temperature (about 20° to 30°C) is convenient from a practical standpoint. Suitable inert solvents which can be used include water, alcohols such as methanol, ethanol, etc.; aromatic hydrocarbons such as benzene, toluene, etc.; halogenated aliphatic hydrocarbons such as chloroform, dichloromethane, 1,2-dichloroethane, etc.; ketones such as acetone, methyl ethyl ketone, methyl isobutyl ketone; and the like. A suitable concentration of the compound of the formula (IV) in the inert solvent can range from about 1 to 50% by weight. The amount of the peroxide employed will depend on the particular peroxide used but can be used in an amount which is sufficient for oxidation of the compound of the formula (IV) to the sulfoxide but not sufficient for oxidation to the sulfone, with generally a molar ratio of 1:1 to 10:1 of the peroxide to the compound of the formula (IV) being suitable.

The phosphoramide derivatives of penicillin represented by the formula (IV) are novel compounds and can be prepared by the reaction of a dialkylhalophosphate with a 6-aminopenicillanic acid or its derivative:

Method (2)

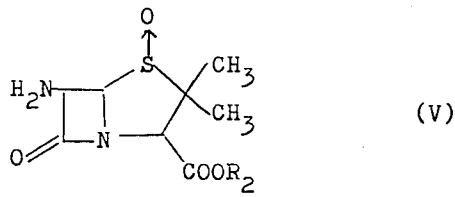

(V)

6-Aminopenicillanic acid (hereinafter referred to as 6-APA) sulfoxide derivatives represented by the formula (V), wherein $R_2$ is as defined above, are allowed to react with a dialkylhalophosphate represented by the formula (VI),

wherein $R_1$ is as defined above, and X represents a halogen atom such as bromine or chlorine in an inert solvent as described for method (1) above, at a temperature at which the decomposition of the β-lactam ring does not occur, with a temperature ranging from about −40°C to room temperature being convenient from a practical standpoint. A suitable amount of the dialkylhalophosphate of the formula (VI) to the 6-APA of the formula (V) ranges from more than an equimolar amount to a small excess, e.g., about 1:1.3, with preferably a small excess of the dialkylhalophosphate of the formula (VI) being used. The addition of a base such as an organic base such as pyridine, quinoline, diethylaniline, dimethylaniline, triethylamine and the like or an inorganic base such as sodium carbonate, sodium bicarbonate and the like as an acid acceptor can be advantageously employed. A suitable amount of the acid acceptor can range from preferably more than 1 mole to 1.3 mole of the acid acceptor per mole of the dialkylhalophosphate of the formula (VI).

6-APA sulfoxide derivatives represented by the formula (V) are novel compounds and can be prepared as follows. Penicillin-G (or -V) sulfoxide derivatives of the formula (VII)

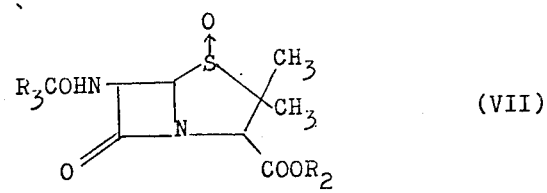

(VII)

wherein $R_3$ is a $C_6H_5CH_2$— group or a $C_6H_5OCH_2$— group, and $R_2$ is as defined above, is treated with a phosphorus halide such as a phosphorus pentahalide, e.g., phosphorus pentachloride, or a phosphorus oxyhalide, e.g., phosphorus oxychloride, in an inert solvent in the presence of a base to obtain the corresponding iminohalide, which is then treated with a lower alcohol to obtain the corresponding iminoether. The iminoether thus obtained is hydrolyzed with water to obtain 6-APA sulfoxide derivatives of the formula (V). Suitable examples of inert solvents are halogenated aliphatic hydrocarbons such as 1,2-dichloroethane, chloroform, dichloromethane, etc., aromatic hydrocarbons such as toluene, etc., esters such as ethyl acetate, etc., and the like. The phosphorus halide is generally used in an excess amount, preferably in an excess amount of greater than 2 moles up to about 5 moles per mole of the penicillin derivative. A preferred reaction temperature ranges from about −40°C to 0°C. Suitable examples of bases as which can be used as acid acceptors are tertiary amines, for example, pyridine, quinoline, diethylaniline, dimethylaniline, etc. The base can be suitably used in an amount of more than about 1 mole up to about 5 moles per mole of the compound of the formula (VII). The iminohalide thus obtained can be isolated, however generally the reaction mixture is treated with an excess amount of the alcohol to produce the corresponding iminoether. Suitable examples of lower alcohols are alcohols having 1 to 4 carbon atoms such as methanol, ethanol, iso-propanol, n-butanol and the like. A suitable amount of the lower alcohol which can be used ranges from more than about 5 up to about 100 to 200 moles per mole of the iminohalide. The reaction proceeds smoothly in the same temperature range as the iminohalidation described above. The hydrolysis is preferably carried out at relatively low temperatures at which the decomposition of the β-lactam ring does not occur, and temperatures ranging from about −10°C to 10°C are convenient from a practical standpoint.

Method (3)

Penicillin-G (or -V) sulfoxide derivatives are allowed to react with a phosphorus halide such as a phosphorus pentahalide, e.g., phosphorus pentachloride, or a phosphorus oxyhalide, e.g., phosphorus oxychloride, followed by reaction with a lower alcohol, e.g., having 1 to 4 carbon atoms as described above to produce the corresponding iminoether which is treated with an alkali. The reaction of penicillin-G (or -V) sulfoxide derivatives with the phosphorus halide is conducted in an inert anhydrous solvent in the presence of a tertiary amine base as an acid acceptor. Suitable examples of these inert solvents are halogenated aliphatic hydrocarbons such as 1,2-dichloroethane, chloroform, dichloromethane, etc., aromatic hydrocarbons such as toluene, etc., esters such as ethyl acetate, etc., and the like. The phosphorus halide is generally used in an excess amount, preferably in an excess amount of greater than 2 moles up to about 5 moles per mole of the penicillin derivative. A preferred reaction temperature ranges from about −40°C to 0°C. Suitable examples of bases which can be used as an acid acceptor are, for example, tertiary amines such as pyridine, quinoline, diethylaniline, dimethylaniline, etc. The base can be suitably used in an amount of more than about 1 mole up to about 5 moles per mole of the compound of the formula (VII). The iminohalide thus obtained can be isolated, however, generally the reaction mixture is treated with an excess amount of a lower alcohol to produce the corresponding iminoether. A suitable amount of the lower alcohol which can be used ranges from more than about 5 up to about 100 to 200 moles per mole of the iminohalide. Suitable examples of lower alcohols having 1 to 4 carbon atoms are methanol, ethanol, isopropanol, n-butanol and the like. The reaction proceeds smoothly in the same temperature range as the iminohalidation described above. The iminoether thus obtained, without isolation, is treated with an excess amount of a base to yield the phosphoramide derivative represented by the formula (III). Typical examples of bases are organic bases such as tertiary amines, e.g., pyridine, quinoline, diethylaniline, dimethylaniline, triethylamine, and the like, or inorganic bases such as sodium bicarbonate, sodium carbonate and the like. A suitable amount of the base which can be used ranges from about 1:1 to about 50:1 to the iminoether.

Furthermore, the compound of the formula (II) can also be obtained by treating the cephalosporanic acid derivatives of the formula (I) with a dialkylhalophosphate of the formula (VI) as described hereinbefore.

The present invention will be illustrated in greater detail by reference to the following examples, which are given only for the purposes of illustration and the invention is not to be interpreted as being limited thereto. Unless otherwise indicated, all parts, percents, ratios and the like are by weight.

EXAMPLE 1

In 20 g of a 85% ortho-phosphoric acid was dissolved 4.5 g of 2,2,2-trichloroethyl 3-methyl-7β-dimethyl-phosphoramido-ceph-3-em-4-carboxylate, and the solution was kept at room temperature for 40 hours while stirring. After completion of the reaction, 100 ml of water was added to the reaction mixture which was then washed with benzene. The separated aqueous layer was neutralized with sodium bicarbonate and extracted with benzene. The benzene layer was washed with water, dried over anhydrous magnesium sulfate and concentrated under reduced pressure to provide 3.3 g of 2,2,2-trichloroethyl 3-methyl-7β-amino-ceph-3-em-4-carboxylate as a slightly yellow solid.

The product thus obtained agreed completely with an authentic sample using thin layer chromatography (referred to as TLC hereinafter).

IR: $\gamma_{max}$ (CHCl$_3$) 1780, 1740 cm$^{-1}$
NMR (CDCl$_3$): δ2.18 ppm (3-CH$_3$)

| Elemental Analysis | C | H | N | S | Cl |
|---|---|---|---|---|---|
| Calculated for C$_{10}$H$_{11}$N$_2$SCl$_3$ (%) | 34.75 | 3.21 | 8.11 | 9.28 | 30.77 |
| Found (%) | 34.65 | 3.13 | 7.96 | 9.40 | 30.53 |

One gram of the product thus obtained was dissolved in ethyl acetate, and a solution of p-toluenesulfonic acid in ethyl acetate was added thereto. The precipitated crystals were filtered to obtain 1.3 g of 2,2,2-trichloroethyl 3-methyl-7β-amino-ceph-3-em-4-carboxylate p-toluenesulfonate in the form of white crystals.
M.P.: 192° − 194°C (decomp.)
IR: $\gamma_{max}$ (Nujol) 1775, 1725 cm$^{-1}$

EXAMPLE 2

In 10 g of polyphosphoric acid was dissolved 2.0 g of 2,2,2-trichloroethyl 3-methyl-7β-dimethylphosphoramide-ceph-3-em-4-carboxylate, and the solution was kept at 35° to 40°C for 12 hours while stirring. After completion of the reaction, 50 ml of water was added to the reaction solution which was then treated in the same manner as described in Example 1 to obtain 1.5 g of 2,2,2-trichloroethyl 3-methyl-7β-amino-ceph-3-em-4-carboxylate. The product thus obtained had the same IR and NMR spectra as in Example 1.

EXAMPLE 3

In 10 g of polyphosphoric acid was dissolved 2.5 g of p-nitrobenzyl 3-methyl-7β-dimethylphosphoramido-ceph-3-em-4-carboxylate, and the solution was kept at 50° to 55°C for 2 hours while stirring.

After adding 80 ml of water to the reaction solution, the solution was neutralized with sodium bicarbonate and extracted with dichloromethane. The separated dichloromethane layer was washed with water, dried over anhydrous magnesium sulfate and concentrated under reduced pressure to obtain 1.9 g of p-nitrobenzyl 3-methyl-7β-amino-ceph-3-em-4-carboxylate as slightly yellow crystals. The product was recrystallized from dichloromethaneethyl acetate to obtain 1.6 g of white crystals. The product thus obtained agreed completely with an authentic sample using TLC.
M.P.: 175° − 177°C

| Elemental Analysis | C | H | N | S |
|---|---|---|---|---|
| Calculated for C$_{15}$H$_{15}$N$_3$O$_5$S (%) | 51.57 | 4.33 | 12.03 | 9.18 |
| Found (%) | 51.50 | 4.40 | 11.95 | 0.06 |

IR: $\gamma_{max}$ (Nujol) 1773, 1702 cm$^{-1}$
NMR (CDCl$_3$): δ2.16 ppm (3-CH$_3$)

EXAMPLE 4

In 10 g of a 85% ortho-phosphoric acid was dissolved 2.0 g of 2,2,2-trichloroethyl 3-methyl-7 β-dimethyl-phosphoramido-ceph-3-em-4-carboxylate, and the solution was kept at room temperature for 48 hours while stirring. Then, after adding 60 ml of water and then 20 ml of a 10% aqueous solution of β-naphthalenesulfonic acid to the reaction solution, the mixture was stirred for 5 hours under ice-cooling. The precipitated crystals were filtered, washed with water and then diethyl ether, and dried under reduced pressure to obtain 2.2 g of 2,2,2-trichloroethyl 3-methyl-7β-amino-ceph-3-em-4-carboxylate β-naphthalenesulfonate as white crystals.

M.P.: 190° – 192°C (decomp.)

| Elemental Analysis | C | H | N | S | Cl |
| --- | --- | --- | --- | --- | --- |
| Calculated for $C_{20}H_{19}N_3O_6S_2Cl_3$ (%) | 43.37 | 3.46 | 5.06 | 11.58 | 19.21 |
| Found (%) | 43.10 | 3.53 | 5.22 | 11.60 | 19.50 |

IR: $\gamma_{max}$ (Nujol) 1775, 1725 cm$^{-1}$

EXAMPLE 5

To 4.5 g of 2,2,2-trichloroethyl 3-methyl-7β-dimethyl-phosphoramido-ceph-3-em-4-carboxylate was added 20 g of a 70% aqueous solution of phosphorous acid, and the mixture was kept at room temperature for 50 hours while stirring. Then the reaction solution was neutralized with a saturated aqueous solution of sodium bicarbonate and extracted with ethyl acetate. The separated ethyl acetate layer was washed with water, dried over anhydrous magnesium sulfate and then a solution of p-toluenesulfonic acid in ethyl acetate was added thereto. The precipitated crystals were filtered to obtain 4.4 g of 2,2,2-trichloroethyl 3-methyl-7β-amino-ceph-3-em-4-carboxylate p-toluenesulfonate as white crystals.

M.P.: 193° – 195°C (decomp.)

The product thus obtained had the same IR spectrum as in Example 1.

EXAMPLE 6

To 1 g of p-nitrobenzyl 3-methyl-7β-diethylphosphoramido-ceph-3-em-4-carboxylate were added 10 ml of dichloromethane and 1 g of an 85% aqueous solution of ortho-phosphoric acid, and the mixture was kept at room temperature for 50 hours while stirring. After completion of the reaction, 5 ml of water was added to the reaction solution which was then treated in the same manner as described in Example 3 to obtain 0.5 g of p-nitrobenzyl 3-methyl-7β-amino-ceph-3-em-4-carboxylate. The product thus obtained had the same IR and NMR spectra as in Example 3.

M.P.: 175° – 176°C

EXAMPLE 7

One gram of 2,2,2-trichloroethyl 3-methyl-7β-diethylphosphoramido-ceph-3-em-4-carboxylate was dissolved in 7 g of a 1:1 by weight mixture of monomethyl phosphate to dimethyl phosphate, and the solution was continuously stirred at 40° to 50°C until the spot of the above phosphoramido cephalosporin derivative was no longer observed on a silica gel TLC using ethyl acetate as a solvent. Thereafter the reaction solution was treated in the same manner as described in Example 1 to obtain 2,2,2-trichloroethyl 3-methyl-7β-amino-ceph-3-em-4-carboxylate as a slightly yellow solid. The product thus obtained had the same IR and NMR spectra as in Example 1.

EXAMPLE 8

In 10 g of polyphosphoric acid were dissolved 2.5 g of p-nitrobenzyl 3-methyl-7β-dimethylphosphoramido-ceph-3-em-4-carboxylate, and the solution was kept at 40° to 45°C for 4 hours while stirring. Then, after adding 50 ml of water to the reaction solution, 3 g of powdered zinc was added at room temperature, followed by stirring for another hour at room temperature. After filtering off the insoluble material, the filtrate was neutralized to a pH of 6 with sodium bicarbonate. After removing again the resulting precipitates, the solution was adjusted to a pH of 4 with conc. hydrochloric acid and allowed to stand overnight in a refrigerator. The precipitated crystals were filtered to obtain 0.9 g of 3-methyl-7β-amino-ceph-3-em-4-carboxylic acid. The product thus obtained agreed completely with an authentic sample on TLC and in the IR spectrum.

M.P.: 230° – 231°C (decomp.)

| Elemental Analysis: | C | H | N | S |
| --- | --- | --- | --- | --- |
| Calculated for $C_8H_{10}N_2O_3S$ (%) | 44.85 | 4.70 | 13.08 | 15.00 |
| Found (%) | 44.74 | 4.83 | 13.20 | 14.87 |

EXAMPLE 9

In 12 g of polyphosphoric acid was dissolved 4.4 g of phenacyl 3-methyl-7β-dimethylphosphoramido-ceph-3-em-4-carboxylate, and the solution was kept at room temperature for 15 hours while stirring.

After adding 100 ml of water, the reaction solution was adjusted to a pH of 6 with a 20% aqueous sodium hydroxide solution and extracted with ethyl acetate. The separated ethyl acetate layer was washed with water, 2 ml of conc. hydrochloric acid was added dropwise therein at 0° to 5°C and then the mixture was kept at the same temperature for 8 hours while stirring. The precipitated crystals were filtered to obtain 3.5 g of phenacyl 3-methyl-7β-amino-ceph-3-em-4-carboxylate hydrochloride.

M.P.: 179° – 180°C

| Elemental Analysis: | C | H | N | S | Cl |
| --- | --- | --- | --- | --- | --- |
| Calculated for $C_{16}H_{17}N_2O_4SCl$ (%) | 52.10 | 4.65 | 7.60 | 8.69 | 9.61 |
| Found (%) | 52.01 | 4.67 | 7.66 | 8.85 | 9.83 |

IR: $\gamma_{max}$ (Nujol) 1780, 1725, 1695 cm$^{-1}$

To 40 ml of formic acid were added 7.4 g of the product thus obtained and 4 g of powdered zinc. The reaction mixture was stirred at room temperature for 2 hours and then filtered. The filtrate was concentrated under reduced pressure and the resulting residue was diluted with 20 ml of water, neutralized to a pH of 4 by addition of a 3N aqueous sodium hydroxide solution and stirred at 0° to 5°C for 5 hours. The precipitate was filtered and washed successively with 10 ml of water and 20 ml of acetone to obtain 3.9 g of 3-methyl-7β-aminoceph-3-em-4-carboxylic acid. The product thus obtained had the same IR and NMR spectra as those of an authentic sample.

M.P.: 232° – 3°C (decomp.)

EXAMPLE 10

Two grams of benzhydryl 3-methyl-7β-dimethylphosphoramido-ceph-3-em-4-carboxylate was dissolved in 10 ml of dichloromethane, and after adding 6 g of polyphosphoric acid thereto, the solution was kept at room temperature for 25 hours while stirring.

Then, after adding 50 ml of water to the reaction solution, the solution was adjusted to a pH of 4 with a 20% aqueous sodium hydroxide solution and kept at 0° to 5°C for 5 hours while stirring. The precipitated crystals were filtered and washed with water and then acetone to obtain 0.56 g of 3-methyl-7β-amino-ceph-3-em-4-carboxylic acid. The product thus obtained agreed completely with an authentic sample on TLC and in the IR spectrum.

M.P.: 233°C (decomp.)

| Elemental Analysis | C | H | N | S |
|---|---|---|---|---|
| Calculated for $C_8H_{10}N_2O_3S$ (%) | 44.85 | 4.70 | 13.08 | 15.00 |
| Found (%) | 44.59 | 4.90 | 12.91 | 14.90 |

EXAMPLE 11

To 5 g of p-nitrobenzyl 6β-dimethylphosphoramido penicilanate 1-oxide were added 25 ml of toluene and 0.2 g of pyridinium phenylphosphate, and the mixture was heated under reflux for 4 hours during which the water formed was separated using a Dean-Stark trap.

After the reaction mixture was cooled to room temperature, 15 g of polyphosphoric acid was added and the resulting mixture was stirred for 15 hours. The mixture was diluted with 100 ml of water, and neutralized to a pH of 6 by the addition of sodium bicarbonate. The precipitate was collected by filtration, washed with water and then a small amount of dichloromethane to obtain 2.9 g of p-nitrobenzyl 3-methyl-7β-amino-ceph-3-em-4-carboxylate. The product thus obtained had the same IR spectrum as in Example 3.

M.P.: 175° – 177°C

REFERENCE EXAMPLE 1

Eight grams of 2,2,2-trichloroethyl 6β-(phenylacetamido)-penicillanate 1-oxide (which can be prepared as disclosed in German Pat. (OLS) No. 2,024,359) was dissolved in 200 ml of dichloromethane, and the solution was cooled to −20°C. Diethylaniline (7.5 g) was added and subsequently a solution of 6.9 g of phosphorus pentachloride in 60 ml of dichloromethane was added dropwise thereto at −20°C, and the resulting mixture was stirred for 2 hours at the same temperature. Furthermore, 80 ml of methanol was added dropwise thereto at −20° to −15°C over a 15 minute period, and the reaction solution was stirred for another 3 hours at the same temperature.

Forty-two grams of sodium bicarbonate were added to the reaction solution which was stirred at 0° to 5°C for 14 hours and then filtered. The filtrate was washed successively with 1 N aqueous hydrochloric acid and a saturated aqueous sodium bicarbonate solution. The separated dichloromethane layer was concentrated under reduced pressure to obtain 12.1 g of the residue. The residue was triturated successively with petroleum ether and diethyl ether to obtain 6.8 g of 2,2,2-trichloroethyl 6β-dimethylphosphoramidopenicillanate 1-oxide.

M.P.: 129.5° – 131°C

IR: $\gamma_{max}$ (Nujol) 1800, 1765 cm$^{-1}$

| Elemental Analysis: | C | H | N | S | Cl | P |
|---|---|---|---|---|---|---|
| Calculated for $C_{12}H_{18}N_2O_7SCl_3P$ (%) | 30.55 | 3.85 | 5.94 | 6.80 | 22.55 | 6.57 |
| Found (%) | 30.65 | 3.67 | 5.77 | 6.76 | 22.32 | 6.38 |

In 30 ml of dry dioxane was dissolved 6.0 g of the product thus obtained, and after adding 0.12 g of pyridinium dichloromethane phosphonate, the solution was heated under reflux for 6 hours during which the condensed liquor was recycled to the reaction system through a Soxhlet extractor packed with molecular sieves.

After the reaction was completed, the reaction solution was concentrated under reduced pressure. The residue thus obtained was dissolved in benzene and the solution was washed successively with 1 N aqueous hydrochloric acid and a saturated aqueous sodium bicarbonate solution, dried over anhydrous magnesium sulfate and concentrated under reduced pressure. The residue was triturated with petroleum ether to yield 4.7 g of 2,2,2-trichloroethyl 3-methyl-7β-dimethylphosphoramido-ceph-3-em-4-carboxylate.

M.P.: 87° – 89°C

Optical Rotation: $[\alpha]_d^{20}$ + 73° (c=1, CHCl$_3$)

IR: $\gamma_{max}$ (Nujol) 1790, 1760 cm$^{-1}$

NMR (CDCl$_3$): δ2.22 ppm (3-CH$_3$)

| Elemental Analysis: | C | H | N | S | Cl | P |
|---|---|---|---|---|---|---|
| Calculated for $C_{12}H_{16}N_2O_6SCl_3P$ (%) | 31.77 | 3.55 | 6.18 | 7.07 | 23.45 | 6.83 |
| Found (%) | 31.61 | 3.70 | 6.01 | 7.30 | 23.30 | 6.70 |

REFERENCE EXAMPLE 2

Ten grams of phenacyl 6-aminopenicillanate hydrochloride (which can be prepared as disclosed in Acta Chemica Scandinavica 21, 2210 (1967)) was suspended in 100 ml of dichloromethane and the suspension was cooled to 0° to 5°C while stirring. Triethylamine (2.7 g)

was added and subsequently 4 g of dimethylchlorophosphate was added over a 20 minute period and the resulting mixture was stirred at the same temperature for 2 hours and at room temperature for another hour.

Thereafter, the reaction solution was washed with dilute aqueous hydrochloric acid and a saturated aqueous sodium bicarbonate solution, and 5 g of m-chloroperbenzoic acid was added over about 10 minutes to the separated organic layer followed by stirring at the same temperature for 10 minutes. The reaction solution was washed with a saturated aqueous sodium bicarbonate solution, dried over anhydrous magnesium sulfate and concentrated to obtain 11.3 g of phenacyl 6β-dimethylphosphoramido-penicillanate 1-oxide in a powder form.

IR: $\gamma_{max}$ (CHCl$_3$) 1800, 1770, 1705 cm$^{-1}$

In 100 ml of dioxane were dissolved 10 g of the product thus obtained, and, after adding 0.5 g of pyridinium dichloromethanephosphonate, the solution was heated under reflux for 6 hours during which the condensed liquor was returned to the reaction system through a Soxhlet extractor packed with molecular sieves. After completion of the reaction, the reaction solution was concentrated under reduced pressure.

The resulting residue was dissolved in dichloromethane and the solution was washed successively with 1 N aqueus hydrochloric acid and a saturated aqueous sodium bicarbonate solution, dried over anhydrous magnesium sulfate and then concentrated under reduced pressure. The residue thus obtained was triturated in petroleum ether to obtain 9 g of phenacyl 3-methyl-7β-dimethylphosphoramido-ceph-3-em-4-carboxylate.

IR: $\gamma_{max}$ (Nujol) 1780, 1730, 1685 cm$^{-1}$

The product thus obtained had a melting point of 177° to 179°C when recrystallized from iso-propyl alcohol.

REFERENCE EXAMPLE 3

To a solution of 10 g of phenacyl 6β-aminopenicillanate in 100 ml of dichloromethane was added portionwise 5.4 g of m-chloroperbenzoic acid at 0° to 5°C over a 20 minute period. The reaction mixture was stirred at the same temperature for another 10 minutes and then washed with a saturated aqueous sodium carbonate solution. The separated dichloromethane layer was dried (MgSO$_4$) and concentrated under reduced pressure to obtain 10.2 g of phenacyl 6β-aminopenicillanate 1-oxide as an amorphous solid.

IR: $\gamma_{max}$ (Nijol) 1775, 1760, 1700 cm$^{-1}$

To a mixture of 100 ml of dichloromethane, 10 g of the product thus obtained and 5 g of diethylaniline was added 4.5 g of dimethyl chlorophosphate at 0° to 5°C over a 10 minute period with stirring. The mixture was stirred at the same temperature for 3 hours, washed with 1N aqueous hydrochloric acid and an aqueous sodium bicarbonate solution, dried (MgSO$_4$) and concentrated under reduced pressure to obtain 13 g of phenacyl 6β-dimethylphosphoramidopenicillanate 1-oxide as an amorphous solid. The product thus obtained had the same IR spectrum as in Reference Example 2.

Using the same procedure as described in Reference Example 2 using 10 g of the product thus obtained, 8.8 g of phenacyl 3-methyl-7β-dimethylphosphoramidoceph-3-em-4-carboxylate was obtained as an amorphous solid. The product thus obtained had the same IR spectrum as in Reference Example 2.

While the invention has been described in detail and with reference to specific embodiments thereof, it will be apparent to one skilled in the art that various changes and modifications can be made therein without departing from the spirit and scope thereof.

What is claimed is:

1. A process for producing a cephalosporanic acid derivative of the formula (I)

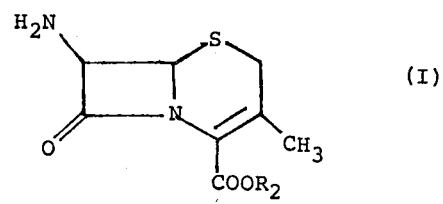

wherein R$_2$ is a hydrogen atom or an ester protective group selected from the group consisting of a methyl group, a 2,2,2-trichloroethyl group, a benzyl group, a p-nitrobenzyl group, a 4-methoxy-3,5-di-tert-butylbenzyl group, a phenacyl group, a methyl sulfonylethyl group, a benzhydryl group and a trimethylsilyl group, which comprises the step of reacting at about 0° to 100°C a phosphoramide derivative of cephalosporin of the formula (II)

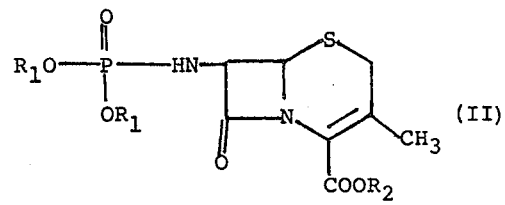

wherein R$_1$ is a lower alkyl group having 1 to 4 carbon atoms and R$_2$ is as defined above, with a phosphorus acid selected from the group consisting of:
 a. orthophosphoric acid;
 b. a phosphoric ester selected from the group consisting of monomethyl phosphate, dimethyl phosphate, monoethyl phosphate, monophenyl phosphate, diphenyl phosphate and monobenzyl phosphate;
 c. phosphorous acid;
 d. a phosphorous ester selected from the group consisting of monoethyl phosphite and monophenyl phosphite;
 e. a phosphoric acid anhydride selected from the group consisting of pyrophosphoric acid, polyphosphoric acid and phosphorus pentoxide;
 f. a phosphoric ester anhydride selected from the group consisting of dimethyl pyrophosphate, diphenyl pyrophosphate and polyphosphoric ester;

g. a phosphonic acid selected from the group consisting of methylphosphonic acid and phenylphosphonic acid;
h. a phosphinic acid selected from the group consisting of dimethylphosphinic acid and diphenylphosphinic acid; and
i. polyphosphoric acid wherein said reacting is in a mixture of said derivative of the formula (II) and said phosphorus acid or in a solution or suspension in an inert solvent of said derivative of the formula (II) and said phosphorus acid.

2. The process according to claim 1, wherein said inert solvent is benzene, toluene, dichloromethane, chloroform, dioxane, diethyl ether, methanol, dimethylformamide, water or acetic acid.

3. The process according to claim 1, wherein the amount of said material is greater than 1 mole of said material per mole of the compound of the formula (II).

4. The process according to claim 1, including recovering the compound of the formula (I) by neutralizing with an inorganic or organic alkaline material selected from the group consisting of sodium bicarbonate, sodium carbonate, sodium hydroxide, ammonia and triethylamine followed by extracting with an inert solvent or by acidifying to precipitate a salt of the compound of the formula (I) and recovering the precipitate.

5. A process for producing a compound of the formula (I)

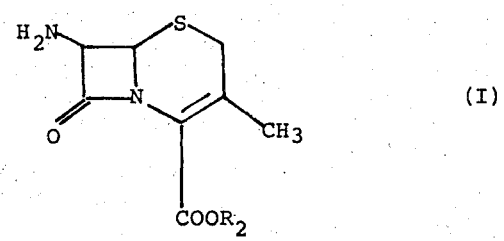

wherein $R_2$ is a hydrogen atom or an ester protective group selected from the group consisting of a methyl group, a 2,2,2-trichloroethyl group, a benzyl group, a p-nitrobenzyl group, a 4-methoxy-3,5-di-tert-butylbenzyl group, a phenacyl group, a methyl sulfonylethyl group, a benzhydryl group and a trimethylsilyl group, which comprises the step of firstly heating a compound of the formula (III):

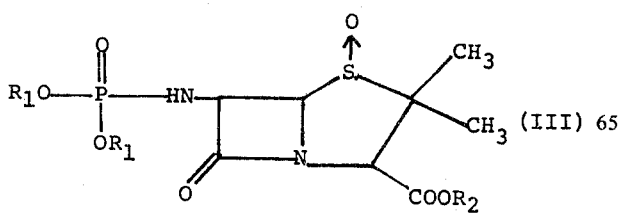

in the presence of an inert solvent at a temperature ranging from about room temperature to the reflux temperature of the inert solvent wherein $R_1$ is a lower alkyl group having 1 to 4 carbon atoms and $R_2$ is as defined above, in the presence of an acid compound selected from the group consisting of
a. an organic acid selected from the group consisting of an organic sulfonic acid, an organic phosphonic acid or a monoester thereof and an organic carboxylic acid or an anhydride thereof;
b. a mineral acid; and
c. a salt of a strong acid and a weak base wherein said weak base has a pKb greater than about 4
to obtain a compound of the formula (II)

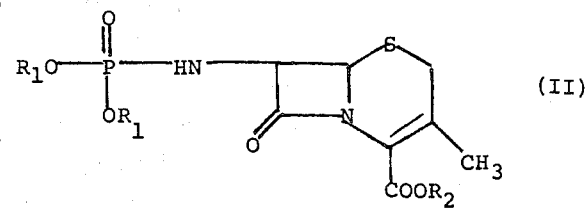

wherein $R_1$ and $R_2$ are each as defined above, and secondly reacting said compound of the formula (II) with a phosphorus acid selected from the group consisting of:
d. orthophosphoric acid;
e. a phosphoric ester selected from the group consisting of monomethyl phosphate, dimethyl phosphate, monoethyl phosphate, monophenyl phosphate, diphenyl phosphate and monobenzyl phosphate;
f. phosphorous acid;
g. a phosphorous ester selected from the group consisting of monoethyl phosphite and monophenyl phosphite;
h. a phosphoric acid anhydride selected from the group consisting of pyrophosphoric acid, polyphosphoric acid and phosphorous pentoxide;
i. a phosphoric ester anhydride selected from the group consisting of dimethyl pyrophosphate, diphenyl pyrophosphate and polyphosphoric ester;
j. a phosphonic acid selected from the group consisting of methylphosphonic acid and phenylphosphonic acid;
k. a phosphinic acid selected from the group consisting of dimethyl phosphinic acid and diphenyl phosphinic acid; and
l. polyphosphoric acid
wherein said reacting is in a mixture of said compound of the formula (II) and said phosphorus acid or in a solution or suspension in an inert solvent of said compound of the formula (II) and said phosphorus acid.

6. The process of according to claim 5, wherein said inert solvent used in said heating step is a solvent which forms an azeotrope with water.

7. The process according to claim 6, wherein said inert solvent is an aromatic hydrocarbon selected from the group consisting of benzene and toluene, dichloroethane, dioxane, acetonitrile, methylisobutylketone or dimethylformamide, or a mixture thereof.

8. The process according to claim 5, including preparing said compound of the formula (III) by the step of oxidizing a phosphoramide derivative of penicillin of the formula (IV)

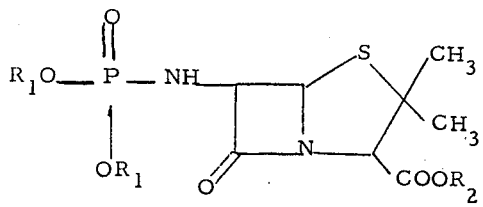

wherein $R_1$ and $R_2$ are as defined in claim 5, with a peroxide selected from the group consisting of peracetic acid, monopermaleic acid, m-chloroperbenzoic acid, sodium peroxide, sodium periodate, hydrogen peroxide and ozone, in an inert solvent.

9. The process according to claim 8, wherein said inert solvent is water, methyl alcohol, ethyl alcohol, benzene, toluene, dichloromethane, 1,2-dichloroethane, chloroform, acetone or methyl isobutyl ketone.

10. The process according to claim 8, wherein said oxidizing is at a temperature of from about −20°C to about room temperature.

11. The process according to claim 5, including preparing said compound of the formula (III) by the step of reacting a 6-aminopenicillanic acid sulfoxide derivative of the formula (V)

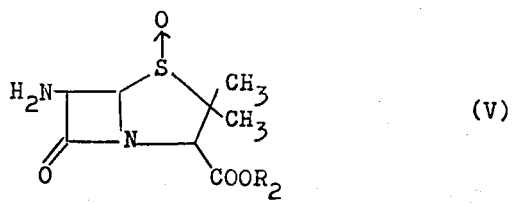

wherein $R_2$ is as defined in claim 5, with a dialkylhalophosphate of the formula (VI)

wherein $R_1$ is as defined in claim 5 and X is a halogen atom in an inert solvent.

12. The process according to claim 11, wherein X is a bromine atom or a chlorine atom.

13. The process according to claim 11, wherein said inert solvent is water, methyl alcohol, ethyl alcohol, benzene, toluene, 1,2-dichloroethane, chloroform, acetone and methyl isobutyl ketone.

14. The process according to claim 11, wherein said reacting is at a temperature ranging from about −40°C to room temperature.

15. The process according to claim 11, wherein said reacting is in the presence of an acid acceptor.

16. The process according to claim 5, including preparing said compound of the formula (III) by the step of reacting a penicillin sulfoxide derivative of the formula (VII)

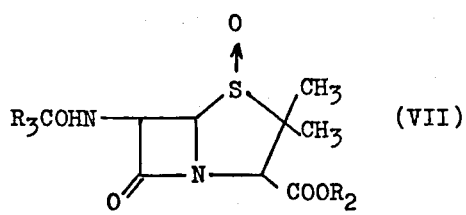

wherein $R_2$ is as defined in claim 11 and $R_3$ is a $C_6H_5CH_2$— group or a $C_6H_5OCH_2$— group with a phosphorus halide in an inert solvent to produce an iminohalide of the penicillin sulfoxide derivative of the formula (VII), reacting said iminohalide with a lower alcohol to produce an iminoether of the penicillin sulfoxide derivative of the formula (VII) and treating said iminoether with a base to produce said compound of the formula (III).

17. The process according to claim 16, wherein said phosphorus halide is a phosphorus pentahalide or a phosphorus oxyhalide.

18. The process according to claim 16, wherein said inert solvent is 1,2-dichloroethane, dichloromethane, chloroform, toluene or ethyl acetate.

19. The process according to claim 16, wherein said reacting with said phosphorus halide and said reacting with said lower alcohol are at a temperature ranging from about −40°C to 0°C.

20. The process according to claim 16, wherein said reacting with said phosphorus halide is in the presence of an acid acceptor.

21. The process according to claim 16, wherein said base is sodium bicarbonate, sodium carbonate, or a tertiary amine.

22. The process according to claim 21, wherein said tertiardy amine is pyridine or quinoline.

* * * * *